(12) United States Patent
Ziegler et al.

(10) Patent No.: US 7,718,406 B2
(45) Date of Patent: May 18, 2010

(54) SUBSTRATES FOR TAFI (A)

(75) Inventors: Hugo Ziegler, Witterswil (CH); Dagmar Prasa, Erfurt (DE); Jörg Stürzebecher, Erfurt (DE); Peter Wikstroem, Gipf-Oberfrick (CH)

(73) Assignee: DSM IP Assets B.V., Heerlen (NL)

( * ) Notice: Subject to any disclaimer, the term of this patent is extended or adjusted under 35 U.S.C. 154(b) by 1013 days.

(21) Appl. No.: 10/530,165

(22) PCT Filed: Dec. 6, 2002

(86) PCT No.: PCT/CH02/00670

§ 371 (c)(1),
(2), (4) Date: Aug. 22, 2005

(87) PCT Pub. No.: WO2004/031216

PCT Pub. Date: Apr. 15, 2004

(65) Prior Publication Data

US 2006/0068457 A1      Mar. 30, 2006

(30) Foreign Application Priority Data

Oct. 4, 2002    (WO) ................... PCT/CH02/00553

(51) Int. Cl.
  *C12P 13/04*   (2006.01)
  *A61K 38/00*   (2006.01)

(52) U.S. Cl. .................... 435/106; 514/2; 424/1.69

(58) Field of Classification Search .............. 514/2
  See application file for complete search history.

(56) References Cited

U.S. PATENT DOCUMENTS 7,119,068 B2 * 10/2006 Greenfield et al. ............ 514/12

OTHER PUBLICATIONS

Bull. Korean. Chem. Soc. 1998, 19(2), 189-193 (cited on specification p. 1, backdrop).*

Tong et al: "Development of substrate forcarboxypeptidase-B by employing thiaarginine peptides" Bulletin of the Korean Chemical Society, Bd. 19, Nr. 2, 1998, Seiten 189-193, XP008018429in der Anmeldung erwAhnt Siehe Seite 189 ("Scheme 1") and Seite192 ("Discussion") {Cited in PCT, Supplied by Applicant;as is Boffa ref. below:].*

Boffa et al: "Plasma and recombinant thrombin-activable fibrinolysis inhibitor (TAFI) and activated TAFI compared with respect to glycosylation, thrombin/thrombomodulin-dependent activation, thermal stability, and enzymatic properties" Journal of Biological Chemistry, Bd. 273, Nr. 4, Jan. 23, 1998, Seiten 2127-2135.*

Hong et al., Development of Substrate for Carboxypeptidase-B by Employing Thiaarginine Peptides; Bull. Korean Chem. Soc, 1998, vol. 19, No. 2, pp. 189-193.

Boffa et al., Plasma and Recombinant Thrombin-activable Fibrinolysis Inhibitor (TAFI) and Activated TAFI Compared with Respect to Glycosylation, Thrombin/Thrombomodulin-dependent Activation, Thermal Stability, and Enzymatic Properties; The Journal of Biological Chemistry, vol. 273, No. 4, Jan. 23, 1998, pp. 2127-2135.

* cited by examiner

*Primary Examiner*—Maury Audet
(74) *Attorney, Agent, or Firm*—Hoffman & Baron, LLP

(57) ABSTRACT

The invention relates to compounds of general formula (I) and acid addition salts thereof, where the various symbols have the meanings given in the description and claims, the production and use thereof as substrate for the detection of TAFIa, a fibrinolysis inhibiting enzyme. The detection occurs by using the absorption between 400 and 412 nm, arising as a result of the formation of 3-carboxy-4-nitrothiophenol from Ellman's reagent as a function of time.

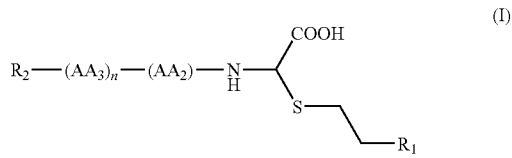

6 Claims, No Drawings

SUBSTRATES FOR TAFI (A)

CROSS-REFERENCE TO RELATED APPLICATIONS

This application is a U.S. National Phase Application of PCT/CH02/000670, filed Dec. 6, 2002, which claims priority to PCT/CH02/00553, filed Oct. 4, 2002, the contents all of which are incorporated herein by reference.

TAFI (thrombin-activatable fibrinolysis inhibitor) is a carboxypeptidase B-like proenzyme of 55 kDa that is activated into the enzyme TAFIa (35 kDa) by proteolysis at Arg-92. Conversely to carboxypeptidase B which is activated as a proenzyme of 46 kDa by proteolysis at Arg-95 and which is active in the stomach and digestive tract, TAFIa is a liver enzyme that is efficient in blood.

TAFIa is formed from TAFI by thrombin and probably also plasmin, and constitutes an important inhibitor of fibrinolysis. Binding of thrombin to thrombomodulin strengthens the activation of TAFI by approx. 1250. The inhibiting effect of TAFIa bases on the capacity to split off carboxy-terminal arginines and lysines, the specificity towards arginine being higher.

TAFIa itself is very sensitive to proteolyses and instable already at 37° C.

Fibrinolysis begins with the conversion of plasminogen into plasmin by tPA. Afterwards, plasmin decomposes the fibrin clot into soluble fibrin products which themselves contribute to further stimulate plasmin formation. TAFIa splits off the carboxy-terminal lysines of these fibrin products, which prevents the formation of the tPA/plasminogen/fibrin complex, thereby inhibiting the fibrinolysis.

Measuring the TAFIa concentration in plasma is very useful to evaluate the bleeding and thrombosis risk of patients.

A determination of carboxypeptidases using immunological tests, such as ELISA for example, is possible, but these tests do not consider the activity of TAFI. Functional tests are described, wherein TAFIa acts on synthetic substrates of the R-Arg-COOH or R-Lys-COOH type, thereby releasing 'R' (e.g. hippuryl) that can be measured by HPLC or spectrophotometry in the near UV range.

There is up to now only one chromogenic assay for the measurement of TAFI and TAFIa in plasma on microtiter plates. The dye formation is however too complicated (several steps) and does not give satisfaction. As the absorption is measured at 490 nm, it is not suitable—like the previously described methods—for determination on usual automates where the extinction variations occur at 405 nm.

The thiaarginine derivatives of the following formulas A and B

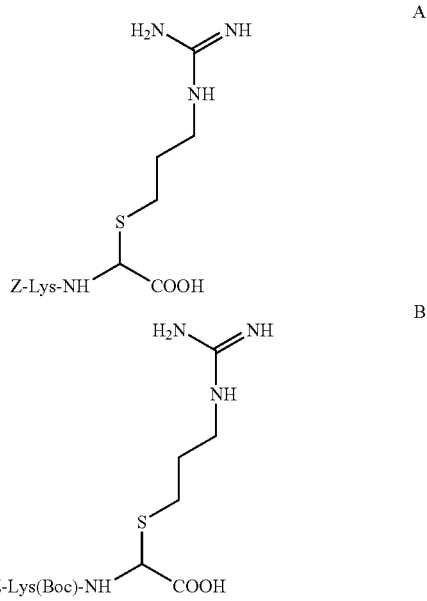

have been described as substrates for carboxypeptidase B (Bull. Korean. Chem. Soc. 1998, 19(2), 189-193). These compounds are remarkably split off by carboxypeptidase B (CPB), but hardly by TAFIa. Detection of CPB by means of compound A is carried out according to the following Scheme 1.

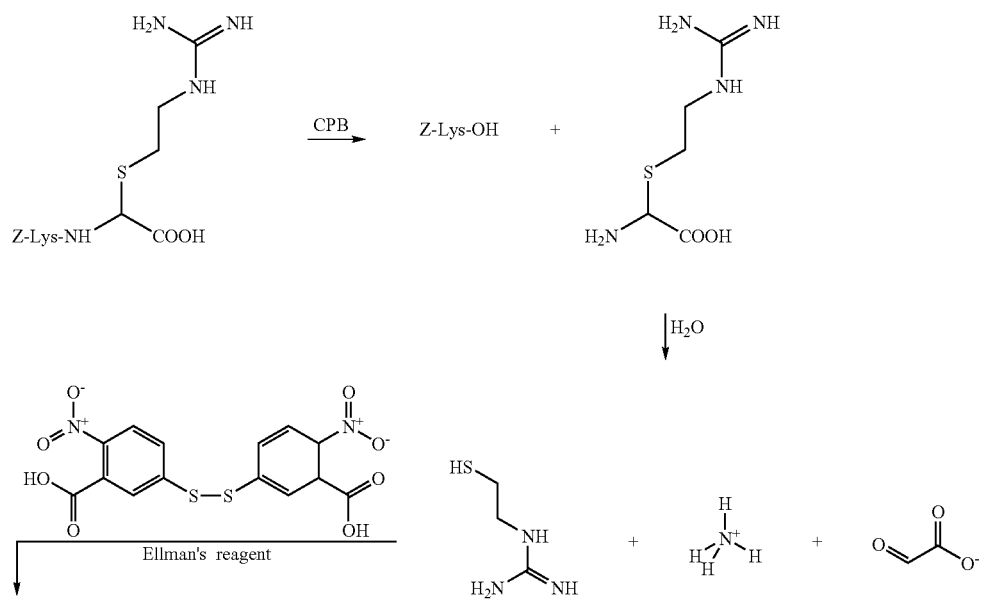

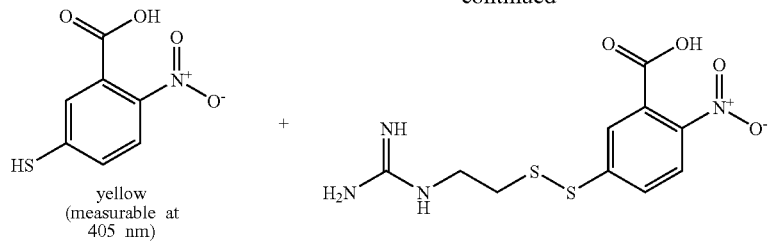

yellow
(measurable at
405 nm)

Surprisingly, this selectivity can be changed in favour of TAFIa already by minor structure variations.

The present invention relates to new TAFIa substrates of the general formula I

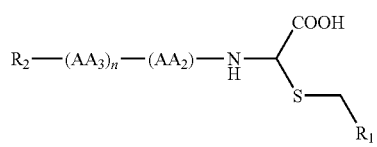

wherein $R_1$ means a $CH_2NH_2$ or $NHC(NH)NH_2$ group, $AA_2$ means non-substituted or substituted lysine, ornithine, arginine or histidine, wherein the substituents are common protective groups, $AA_3$ means a natural amino acid in which a present, protectable group may be substituted with a usual protective group in the side chain, n represents 0 or 1, and $R_2$ means a Bz, Bzl, Ac, Boc, Z, Suc, MeoSuc or Tos group, provided that the following cases do not occur simultaneously: n=0, $R_1$=NHC(NH)NH$_2$, $R_2$=Z and ($AA_2$)=non-substituted or Boc-substituted lysine, as racemates or enantiomeric pure isomers, and the salts thereof with mineral or organic acids.

$R_1$ preferably means NHC(NH)NH$_2$.

The preferred denotations of $AA_2$ may be e.g. Lys(ε-Z), Lys(ε-Boc), Lys(ε-Ac), Lys(ε-Bz), Lys(ε-Bzl), Lys(ε-Tos), Orn(δ-Z), Orn(δ-Boc), Orn(δ-2-chlor-Z), Orn(δ-Dnp), Orn (δ-Z), Orn(δ-Aloc), Arg(ω-Pbf), Arg(δ,ω)-Boc)$_2$, Arg(δ,ω-Z)$_2$, Arg(ω-Tos), His($N^{im}$-Boc), His($N^{im}$-Ac), His($N^{im}$-Bz), His($N^{im}$-Bzl) or His($N^{im}$-Tos), Lys(ε-Z) being particularly preferred.

E.g. tBu, Bzl or Ac can be taken into account as protective groups in the amino acid $AA_3$, wherein phenylalanine, alanine, serine and valine are preferred amino acids.

$R_2$ preferably means Bz or Boc.

E.g. hydrobromides, hydrochlorides, trifluoracetates or acetates can be taken into account as salts, wherein acetate, trifluoracetate and hydrochloride salts are preferred.

The above used abbreviations for protective groups as well as a series of further abbreviations are explained in the table to be found between Example 2 and Example 3.

The compounds of general formula I, which—relating to the asymmetrical carbon with the sulfur-containing substituent—can be present as racemates or in one of their enantiomer-pure configurations D and L, can be manufactured according to the known methods described hereinafter.

Protected amino acids or protected oligopeptide derivatives are converted into the corresponding acid amides, and these are condensed under reflux with an alkyl ester of glyoxylic acid, preferably a $C_{1-6}$ alkyl ester such as ethyl glyoxylate, according to the method described by Hong, N. J. et al., Bull. Korean Chem. Soc. 1998, 19(2), 189-193. The thereby resulting hydroxyglycine derivatives are O-acetylated and substituted with a corresponding mercaptoalkyl compound, such as cystamine, 3-mercaptopropylamine or S-2-aminoethylisothiouronium bromide. Afterwards, the obtained alkylesters of the compounds of formula I are saponified into the corresponding free acids. The enantiomer-pure acids can be obtained through enantioselective hydrolysis of the esters by means of appropriate enzymes.

The compounds of formula I and their acid addition salts are appropriate substrates for the determination of TAFIa. According to the present invention, the determination can be performed by reacting TAFIa in the presence of 5,5'-dithio-bis-(2-nitrobenzoic acid), the so-called "Ellman's Reagent", on a compound according to one of claims 1 to 7 and measuring the absorption between 400 and 412 nm resulting from the formation of 3-carboxy-4-nitrothiophenol as a function of time using a spectrophotometer. The mentioned reaction preferably takes place between approx. 10° C. and 37° C., preferably at room temperature, and the reaction period may last approx. 5 to 15 minutes, preferably about 10 minutes. TAFI present in blood plasma can be used as the source of TAFIa.

The following examples are intended to further explain the present invention without limiting its scope.

The eluates and products obtained according to Examples 1 and 2 were identified and characterized by proton NMR, HPLC electrospray MS and/or elementary analysis.

EXAMPLE 1

Preparation of benzoyl-(L)-lysyl-(ε-benzyloxycarbo-nyl)-α-(D,L)-(2-guanidinoethylthio)-glycine hydrochloride salt [Bz-(L)-Lys(Z)-(D,L)-Gly(α-GUS)—OH.HCl]

1A) Benzoyl-(L)-lysyl(ε-benzyloxycarbonyl)-α-(D, L)-hydroxyglycine-ethylester [Bz-(L)-Lys(Z)-(D,L)-Gly(α-OH)-Oet]

5.0 g (13 mmol) of benzoyl-(L)-lysine amide and a 50% toluene solution of 13.3 g (65 mmol) of ethyl glyoxylate were refluxed in 100 ml of THF. After 4 hours, the solution was cooled to RT and directly converted in the reaction step 1B).

1B) Benzoyl-(L)-lysyl(ε-benzyloxycarbonyl)-α-(D, L)-acetoxyglycine-ethylester [Bz-(L)-Lys(Z)-(D,L)-Gly(α-Oac)-Oet]

The reaction solution from 1A) was mixed with 127 mg (1 mmol) of DMAP, 24.7 ml (0.31 mol) of pyridine and 40 g (0.39 mol) of acetic acid anhydride and stirred for 90 min. at RT. The reaction solution was filtered over silica gel, the solvent was evaporated and the obtained raw product was dried in a vacuum desiccator.

Yield: 14 g.

1C) Benzoyl-(L)-lysyl-(ε-benzyloxycarbonyl)-α-(D,L)-(2-guanidinoethylthio)-glycine ethylester [Bz-(L)-Lys(Z)-(D,L)-Gly(α-GUS)-OEt]

5.5 g (19.5 mmol) of S-(2-aminoethyl)isothiouronium bromide hydrobromide and 4 g (39 mmol) of TEA were dissolved in 50 ml of DMF and stirred for 5 min. at RT. Afterwards, a solution of 14 g of the product obtained under 1B) in 30 ml of DMF was added. After 2 hours of stirring at RT, the solvent was evaporated on a rotovapor. The obtained raw material was chromatographed with LH20 (methanol). The compound precipitated as a yellowish oil.

ESI-MS [M+H]− 587

1D) Benzoyl-(L)-lysyl-(ε-benzyloxycarbonyl)-α-(D,L)-(2-guanidinoethylthio)-glycine hydrochloride salt [Bz-(L)-Lys(Z)-(D,L)-Gly(α-GUS)-OH.HCl]

3.1 g (4.4 mmol) of compound 1C) was dissolved in 20 ml of ethanol, mixed with 11 ml of NaOH (1N) and stirred overnight at RT. After adjustment of the pH to 3 with citric acid and evaporation of the solvent, the residue was chromatographed with LH20 (methanol). For conversion into the hydrochloride salt, the pure, concentrated fractions are dissolved in 100 ml of a methanol/water mixture (1:1) and chromatographed over Amberlite (Cl⁻ form). The obtained solution was concentrated on the rotovapor and the product precipitated as a nearly white, amorphous powder under addition of BME. The powder was filtered off, washed with some BME and dried in a vacuum drier.

Yield: 2.5 g, ESI-MS [M+H]− 559

EXAMPLE 2

Preparation of benzoyl-(L)-lysyl-(ε-benzyloxycarbonyl)-α-(D,L)-(3-aminopropylthio)-glycine trifluoracetic acid salt [Bz-(L)-Lys(Z)-(D,L)-Gly(α-SprA)-OH.TFA]

2C) Benzoyl-(L)-lysyl-(ε-benzyloxycarbonyl)-α-(D,L)-(3-aminopropylthio)-glycine ethylester trifluoracetic acid salt [Bz-(L)-Lys(Z)-(D,L)-Gly(α-SprA)-Oet.TFA]

2.5 g (20 mmol) of 3-mercaptopropylamine hydrochloride and 2 g (20 mmol) of TEA were dissolved in 40 ml of DMF, the solution was stirred for 5 min at RT and added to a solution of 6.9 g of the product obtained under 1B) in 30 ml of DMF. After 2 hours of stirring at RT, the solvent was evaporated on a rotovapor. The obtained raw material was chromatographed by preparative HPLC (ACN/H₂O/TFA). The pure fractions were concentrated on the rotovapor.

ESI-MS [M+H]− 559

2D) Benzoyl-(L)-lysyl-(ε-benzyloxycarbonyl)-α-(D,L)-(3-aminopropylthio)-glycine trifluoracetic acid salt [Bz-(L)-Lys(Z)-(D,L)-Gly(α-SprA)-OH.TFA]

0.43 g (0.6 mmol) of compound 2C) was dissolved in 7 ml of ethanol, mixed with 2 ml of NaOH (1N) and stirred overnight at RT. The reaction solution was adjusted to pH 3 with citric acid 10%, extracted 3 times with 20 ml of ethylacetate and washed twice with saturated NaCl solution. The organic phase was dried over Na₂SO₄, filtered and the solvent was evaporated on the rotovapor. The raw material was chromatographed by preparative HPLC (ACN/H₂O/TFA). The pure fractions were concentrated on the rotovapor, whereupon the residue was dissolved in some methanol and precipitated by addition of BME. The nearly white powder was filtered off, washed with some BME and dried in a vacuum desiccator.

ESI-MS [M+H]− 531

| Abbreviations | |
|---|---|
| Ac | Acetyl |
| ACN | Acetonitrile |
| Aloc | Allyloxycarbonyl |
| BME | t-Butyl methyl ether |
| Boc | t-Butyloxycarbonyl |
| Bz | Benzoyl |
| Bzl | Benzyl |
| DMAP | 4-(Dimethylamino)-pyridine |
| DMF | N,N-Dimethylformamide |
| Dnp | 2,4-Dinitrophenyl |
| DTNB | 5,5'-Dithiobis-(2-nitrobenzoic acid) |
| EtOAc | Ethylacetate |
| GUS | 2-Guanidino-ethyithio |
| HEPES | 4-(2-Hydroxyethyl)-piperazin-1-ethane sulfonic acid |
| LH20 | Sephadex |
| MeoSuc | Methoxysuccinyl |
| NAPAP | Nα-(2-naphthylsulfonyl-glycyl)-4-amidinophenylalanine piperidide |
| Pbf | 2,2,4,6,7-Pentamethyl-dibenzohydrofuran-5-sulfonyl |
| SprA | 3-Aminopropylthio |
| RT | Room temperature |
| Suc | Succinyl |
| tBu | tert.-Butyl |
| TEA | Triethylamine |
| TFA | Trifluoracetic acid |
| THF | Tetrahydrofuran |
| Tos | Tosyl |
| Z | Benzyloxycarbonyl |

EXAMPLE 3

Quantitative Determination of TAFIa

Principle: TAFIa is determined as shown in Scheme 1. In a first step, the substrate is hydrolyzed by TAFIa in such a way that a thioamino acid (thiaarginine or thialysine) is released. These instable intermediates are rapidly decomposed into 2-mercaptoethylguanidine or 3-mercaptopropylamine, respectively. These mercapto compounds react with Ellman's reagent (5,5'-dithio-bis-(2-nitrobenzoic acid)), thereby releasing the strongly yellow 3-carboxy-4-nitrothiophenol that can be measured using a spectrophotometer at 405-412 nm. The free thiol content measured is directly proportional to the quantity of substrate hydrolyzed by TAFIa and thereby allows a quantitative analysis of the enzyme activity.

Enzyme assay: The enzyme activity is measured at room temperature by using a 10 mM substrate stock solution in DMSO. TAFI of human origin can be obtained in a stock solution of 360 µg/ml from Enzyme Research Laboratory or over blood plasma. Activation of TAFI to TAFIa occurred with thrombin (2.7 U/ml), the activation of which was produced with 30 µg of thrombomodulin. Excessive thrombin activity was eliminated by adding the synthetic inhibitor NAPAP. The measurement was performed on microtiter plates.

The absorption increase at 405-412 nm was recorded for 10 minutes.

Activation:

| TAFI | 20 µl |
| Thrombin (2.7 U/ml) | 20 µl |
| Thrombomodulin (30 µg/ml) | 20 µl | in buffer (20 mM HEPES, 5 mM CaCl$_2$, 0.01% Tween 80; pH 7.4)
incubate for 5 min at 25° C.

Measurement:

| Buffer (20 mM HEPES, 5 mM CaCl$_2$, 0.01% Tween 80; pH 7.4) | 120 µl |
| NAPAP (100 µM) | 20 µl |
| DTNB (5 mM) | 10 µl |
| Substrate (10 mM) | 20 µl | measure for 10 min at RT

Results:
Splitting of thiaarginine and thialysine substrates (final concentration 174 µM) by TAFIa (final concentration 17 µg/ml)
in brackets the value for carboxypeptidase B
Substances of comparison A and B from Bull. Korean. Chem. Soc. 1998, 19(2), 189-193
ΔE=Extinction variation at 405 nm

TABLE 1

| No. | Substrate | ΔE/min | |
|---|---|---|---|
| 4269 | Bz-K(Z)-G(GUS)-OH × HCl | 0.108 | (0.018) |
| 4273 | Boc-K(Tos)-G(GUS)-OH × HCl | 0.014 | (0.048) |
| 4275 | Boc-K(Z)-G(GUS)-OH × TFA | 0.041 | (0.028) |
| 4298 | Boc-F-K(Boc)-G(GUS)-OH × HCl | 0.043 | (0.034) |
| 4300 | Bz-P-K(Boc)-G(GUS)-OH × TFA | 0.012 | (0.072) |
| 4302 | Z-A-K(Boc)-G(GUS)-OH × HCl | 0.042 | (0.059) |
| 4334 | Bz-V-G(GUS)-OH × TFA | 0.034 | |
| 4336 | Bz-V-G(α-SPrA)-OH × TFA | 0.053 | |
| 4339 | Bz-K(Z)-G(α-SPrA)-OH × TFA | 0.055 | |
| 4341 | Boc-K(Z)-G(α-SPrA)-OH × TFA | 0.054 | |
| | Substance of comparison A × HCl | 0.002 | (0.062) |
| | Substance of comparison B × HCl | 0.016 | (0.077) |

The invention claimed is:

1. Compounds of general formula I

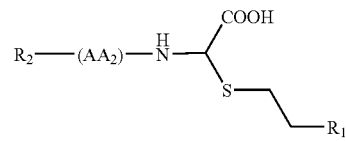

wherein
R$_1$ means a CH$_2$NH$_2$ or NHC(NH)NH$_2$ group,
AA$_2$ means non-substituted or substituted L-lysine, wherein the substituents are common protective groups, and
R$_2$ means a Bz, Bzl, Ac, Boc, Z, Suc, MeoSuc or Tos group,
provided that the following cases do not occur simultaneously: R$_1$=NHC(NH)NH$_2$, R$_2$=Z and (AA$_2$)=non-substituted or Boc-substituted L-lysine,
and the salts thereof with mineral or organic acids.

2. Compounds according to claim 1, wherein AA$_2$ represents L-Lys(ϵ-Z), L-Lys(ϵ-Boc), L-Lys(ϵ-Ac), L-Lys(ϵ-Bz), L-Lys(ϵ-Bzl), L-Lys(ϵ-Tos), or L-Lys(ϵ-Z).

3. Compounds according to claim 1, wherein
R$_1$ means NHC(NH)NH$_2$,
AA$_2$ means L-Lys(ϵ-Z) or L-Lys(ϵ-Boc), and
R$_2$ means Bz, Boc or Z.

4. Compounds according to claim 1, wherein
R$_1$ means CH$_2$NH$_2$,
AA$_2$ means L-Lys(ϵ-Z) or L-Lys(ϵ-Boc), and
R$_2$ means Bz, Boc or Z.

5. Compounds according to claim 1, wherein the compounds are present as acid addition salts in the form of hydrobromides, hydrochlorides, trifluoracetates or acetates.

6. Compounds according to claim 2, wherein the compounds are present as acid addition salts in the form of hydrobromides, hydrochlorides, trifluoracetates or acetates.

* * * * *